United States Patent
Miara et al.

(10) Patent No.: US 9,904,772 B2
(45) Date of Patent: Feb. 27, 2018

(54) SCREENING SOLID STATE IONIC CONDUCTORS FOR HIGH IONIC CONDUCTIVITY

(71) Applicants: Samsung Electronics Co., Ltd., Suwon-si, Gyeonggi-do (KR); Massachusetts Institute of Technology, Cambridge, MA (US)

(72) Inventors: Lincoln J Miara, Cambridge, MA (US); William Richards, Cambridge, MA (US); Shyue Ping Ong, San Diego, CA (US); Yifei Mo, Greenbelt, MD (US); Gerbrand Ceder, Wellesley, CA (US)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 443 days.

(21) Appl. No.: 14/536,506

(22) Filed: Nov. 7, 2014

(65) Prior Publication Data
US 2015/0204809 A1    Jul. 23, 2015

Related U.S. Application Data

(60) Provisional application No. 61/910,576, filed on Dec. 2, 2013.

(51) Int. Cl.
*H01M 10/42* (2006.01)
*G06F 19/00* (2018.01)

(52) U.S. Cl.
CPC ........... *G06F 19/704* (2013.01); *H01M 10/42* (2013.01); *H01M 2300/0065* (2013.01)

(58) Field of Classification Search
None
See application file for complete search history.

(56) References Cited

U.S. PATENT DOCUMENTS

| 6,019,505 A * | 2/2000 | Bonne | G01N 27/18 374/40 |
| 6,234,016 B1 * | 5/2001 | Bonne | G01F 1/6845 73/204.26 |

(Continued)

OTHER PUBLICATIONS

Yingchun Zhang, "Computational study of the transport mechanisms of molecules and ions in solid materials", PhD dissertation submitted to Office of Graduate Studies, Texas A&M University, May 2006.

(Continued)

*Primary Examiner* — Michael Lebentritt
(74) *Attorney, Agent, or Firm* — Cantor Colburn LLP

(57) ABSTRACT

Non-normal statistics applied to diffusivity calculations accelerate screening of ionic conductors for electrochemical devices such as electric storage batteries, fuel cells, and sensors. Displacements of atomic species within a crystalline structure for a candidate ionic conductor material are analyzed using a Skellam distribution optionally combined with Gaussian noise to calculate values for the standard deviation, upper error bound, and lower error bound for predicted values of diffusivity (D). When the predicted values of D have sufficient statistical precision, the diffusivity calculation is terminated and the calculated diffusivity is compared to a threshold value of diffusivity. When the threshold has been exceeded, the candidate ionic conductor may be listed as a preferred good conductor. When the calculated diffusivity fails to exceed the threshold, the material may be listed as a poor conductor and may be eliminated from further consideration.

21 Claims, 3 Drawing Sheets

(56) References Cited

U.S. PATENT DOCUMENTS

| | | | | |
|---|---|---|---|---|
| 6,366,873 | B1* | 4/2002 | Beardmore | G06F 17/5018 700/121 |
| 6,721,664 | B1* | 4/2004 | Terwilliger | G06K 9/00127 702/19 |
| 6,931,329 | B1* | 8/2005 | Terwilliger | G06F 19/16 702/19 |
| 7,424,411 | B2* | 9/2008 | Ito | G06F 17/5018 700/123 |
| 7,756,687 | B2* | 7/2010 | Hwang | G06F 17/5018 438/369 |
| 8,121,431 | B2* | 2/2012 | Hwang | G06T 7/12 382/199 |
| 8,454,748 | B2* | 6/2013 | Iwaki | C07D 487/22 117/201 |
| 8,921,215 | B2* | 12/2014 | Komachi | H01L 21/26513 257/E21.334 |
| 9,064,072 | B2* | 6/2015 | Brown | G06F 17/5036 |
| 2002/0011852 | A1* | 1/2002 | Mandelis | G01R 31/311 324/750.02 |
| 2002/0188373 | A1* | 12/2002 | Goddard, III | G06F 17/5018 700/200 |
| 2003/0205404 | A1* | 11/2003 | Hara | H01B 1/24 174/128.2 |
| 2003/0236655 | A1* | 12/2003 | Govind | G06F 19/702 703/12 |
| 2005/0094141 | A1* | 5/2005 | Zechner | G06F 17/5018 356/338 |
| 2007/0072318 | A1* | 3/2007 | Hwang | G06F 17/5018 438/14 |
| 2008/0301599 | A1* | 12/2008 | Moroz | G06F 17/5036 716/136 |
| 2010/0158392 | A1* | 6/2010 | Adams | B82Y 30/00 382/218 |
| 2011/0161361 | A1* | 6/2011 | Csanyi | G06F 19/704 707/769 |
| 2011/0313748 | A1* | 12/2011 | Li | G06F 17/5045 703/14 |
| 2013/0304434 | A1 | 5/2013 | Miara et al. | |
| 2014/0286478 | A1* | 9/2014 | Paulus | G01N 23/203 378/88 |
| 2015/0192533 | A1* | 7/2015 | Bajaj | G06F 17/5009 702/23 |
| 2017/0018781 | A1* | 1/2017 | Zimmerman | B01J 43/00 |
| 2017/0025705 | A1* | 1/2017 | Miara | H01M 10/0562 |

OTHER PUBLICATIONS

Balbuena, Perla B. et al; "Molecular modeling studies of polymer electrolytes for power sources", Electrochimica Acta (2005),pp. 3788-3795.

* cited by examiner

SCREENING SOLID STATE IONIC CONDUCTORS FOR HIGH IONIC CONDUCTIVITY

CROSS REFERENCE TO RELATED APPLICATIONS

This application claims the benefit of U.S. Provisional Application No. 61/910,576 filed Dec. 2, 2013, incorporated herein by reference in its entirety.

TECHNICAL FIELD

An embodiment relates in general to an ionically conductive material for a device such as an electric storage battery, a fuel cell, or a sensor, and more particularly to selection of a solid state ionic conductor with high ionic conductivity by accelerated simulation of molecular positions and motions.

BACKGROUND

The safety, energy density, output voltage, output current, and service lifetime of an electrical device such as a rechargeable electric storage battery or fuel cell may be improved by elimination of liquid electrolyte from the device. A liquid electrolyte may be toxic, flammable, or have a corrosive effect on other materials. Efforts have been made to remove liquid electrolyte from batteries and other devices by searching for materials which are solid state ionic conductors at room temperature. Materials with high conductivity at room temperature are preferred over materials with low conductivity. A solid state ionic conductor with high conductivity may be referred to as a superionic conductor material. Minimizing material cost is essential for some applications.

The properties of a solid state ionic conductor are influenced by the chemical formulation of the material, the crystalline structure of the material, temperature, and other factors. The number of candidate materials to be screened for use in a target battery, fuel cell, or sensor application may be so high as to make it impractical to synthesize and test more than a tiny fraction of the potential number of materials and crystalline structures. The complexity and time required for previously known numerical simulation strategies and laboratory analytical methods have limited evaluations of candidate materials to fewer than ten per year per researcher.

Computational methods based on molecular dynamics calculations have been used to predict candidate materials to be synthesized and tested for desirable material properties. However, previously known methods suffer from long computational execution times for screening each candidate material, leading to high costs for computer resources. For example, a previously known method for screening a candidate material performs multiple molecular dynamics calculations to calculate a set of diffusivity values "D" until the values of D converge with a preferred value of variance. Convergence may be achieved when a calculated value "2dDt" is greater than a preferred value, for example 60 angstroms, where "d" is the number of spatial dimensions, "t" represents a simulation time, that is, a duration of real-world time being simulated, and D may range in value from $10^{-12}$ cm$^2$/s to $10^{-4}$ cm$^2$/s. Furthermore, previously known methods have applied a normal distribution to the results of molecular dynamics calculations, possibly resulting in inaccurate values for D. Inaccuracies may become worse as simulation time "t" is reduced, for example when reducing a duration of real-world time being simulated to shorten an amount of execution time required to complete a simulation.

Execution times for computer programs using previously known methods for performing calculations to find a material with sufficiently high ionic conductivity for a selected application have been estimated to extend from about 3000 CPU-hours to about $3 \times 10^{10}$ CPU-hours. Even at the lower end of the range of estimated computation execution times, previously known methods are too slow and too expensive in time, computer resources, and human resources to permit evaluation of many different material candidates within acceptable market windows for new consumer, commercial, or industrial products.

SUMMARY

An example of a high ionic conductivity solid state screen method embodiment includes receiving a crystal structure selection for an inorganic material, receiving a threshold value selection for diffusivity, and calculating by a processor a displacement of a selected atomic species in the inorganic material relative to the crystal structure. The method embodiment further includes calculating by the processor an estimate of diffusivity from a Skellam distribution of the displacement, comparing the estimate of diffusivity to the threshold value selection for diffusivity; and when the estimate of diffusivity is greater than or equal to the threshold value selection for diffusivity, identifying the inorganic material as a preferred material.

An example of a high ionic conductivity solid state screening apparatus embodiment includes a processor and a memory couple to the processor. The memory includes instructions executable by the processor to receive a crystal structure selection for an inorganic material; receive a threshold value selection for diffusivity; calculate a displacement of a selected atomic species in the inorganic material relative to the crystal structure; calculate an estimate of diffusivity from a Skellam distribution of the displacement; compare the estimate of diffusivity to the threshold value selection for diffusivity; and identify the inorganic material as a preferred material when the estimate of diffusivity is greater than or equal to the threshold value selection for diffusivity.

An example of a computer program product embodiment includes a non-transient computer-readable storage medium including instructions executable by a processor comprising the steps of receiving a crystal structure selection for an inorganic material; receiving a threshold value selection for diffusivity; and identifying the inorganic material as a preferred material when the estimate of diffusivity is greater than or equal to the threshold value selection for diffusivity.

BRIEF DESCRIPTION OF THE DRAWINGS

Accompanying drawings show one or more embodiments; however, the accompanying drawings should not be taken to limit the invention to only the embodiments shown. Various aspects and advantages will become apparent upon review of the following detailed description and upon reference to the drawings in which.

DESCRIPTION

Figure 1:
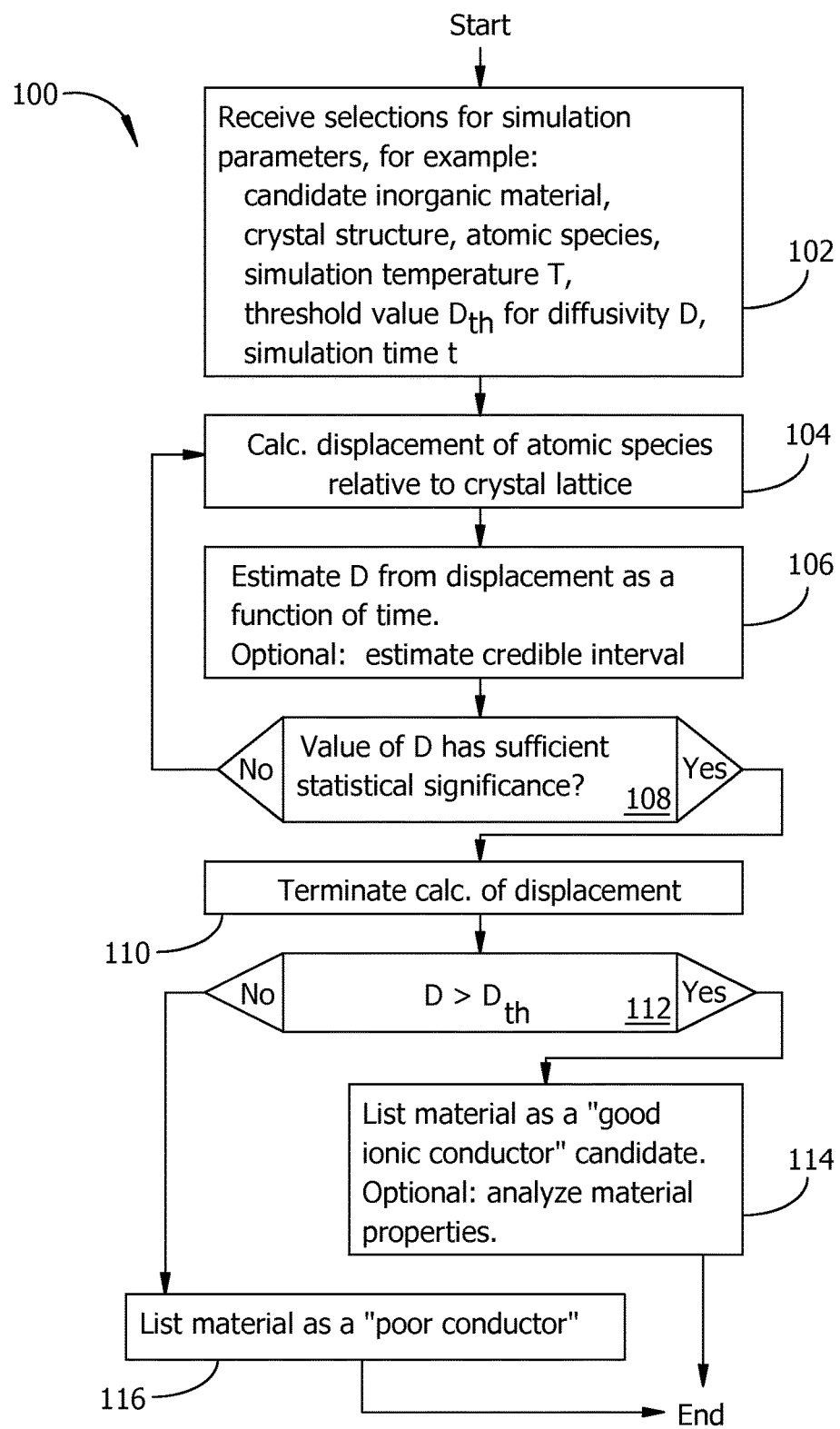
FIG. 1 is a block diagram illustrating an example of a method embodiment.

Calculations of positions and velocities of atoms in a solid state structure are combined with statistical analysis using a non-normal distribution to rapidly screen ionically conductive materials for electrochemical devices such as electric storage batteries, fuel cells, and sensors. An inorganic crystal structure is simulated at a specified temperature for a selected short simulation time to predict displacements of atoms in the structure. An estimate for diffusivity is calculated from displacement data by fitting a model relating atom displacement as a function of time to the data. Upper and lower error bounds for diffusivity may also be calculated. Calculations for the estimate of diffusivity continue until the estimate of diffusivity has sufficient statistical precision. When the estimate of diffusivity has sufficient statistical precision, diffusivity calculations are interrupted and the estimate of diffusivity is compared to a selected threshold value of diffusivity. The candidate ionic conductor is listed as a good conductor when the threshold value of diffusivity has been exceeded, and the candidate material may optionally be subjected to further analysis. When the calculated diffusivity is less than the threshold, the candidate material is listed as a poor conductor and may be eliminated from further analysis.

Some embodiments include a method for selecting a preferred ionic conductor material for use as a solid state ionic conductor in an electrochemical device. A method embodiment identifies preferred structures for subsequent in-depth study including, but not limited to, material synthesis, measurement of physical and electrical properties such as chemical stability, stability under charge and discharge cycles, temperature stability, and so on. Electrical properties such as output voltage, current, and recharge time may be determined for devices using materials selected in accord with a method embodiment.

An example of an apparatus embodiment includes a processor and a memory coupled to the processor. The processor may include a central processing unit implemented in semiconductor hardware devices. The processor retrieves instructions from the memory for performing calculations in accord with the method embodiment. Other embodiments include a computer-program product comprising instructions in accord with the method embodiment. Another embodiment includes an ionically conductive material manufactured by a process in accord with the method embodiment. Yet another embodiment includes an electric storage battery including a solid state ionic conductor in accord with the method embodiment.

Some previously known methods predict candidates for solid state ionically conductive materials from descriptions of the geometry of material. Some previously known methods predict transport of atomic species such as lithium through a solid electrolyte interphase under the influence of an electric field. Other previously known methods use molecular dynamics calculations to model behavior of polymer materials used for electrolytes. However, unlike the examples of embodiments described herein, none of the previously known methods have been applied to a determination of ionic conductivity in inorganic crystal structures using statistical information to accelerate calculations of displacement, velocity, and diffusion for a solid state ionically conductive material.

In contrast to methods previously known in the art, embodiments are well suited to rapidly evaluating thousands of candidate materials at low cost for computer resources by reducing a computational execution time duration for each candidate, much lower costs for laboratory synthesis and analysis of candidate materials, and lower material costs resulting from identification of highly conductive materials that may be manufactured without expensive raw materials such as germanium or materials that may be subject to limited availability. The application of non-normal statistical methods to the acceleration of displacement and diffusion calculations enables accurate displacement information to be calculated by accounting for deviations from Brownian behavior resulting from short simulation times or small simulation sample sizes. Furthermore, an upper bound for diffusivity can be calculated for displacement simulations of any time duration, with good agreement with prior art methods using longer simulation times. Embodiments are therefore well suited for high-throughput screening of candidate materials before synthesis and experimental testing of the materials are performed.

Embodiments may use selected short simulation time durations for calculation of displacements of atomic species in a crystal structure. Selecting a short simulation time reduces computational execution time and enables evaluation of a larger number of candidate materials compared to previously known numerical analytical methods. As used herein, simulation time refers to a selected duration of real-world time over which displacements of atoms in a candidate material are to be calculated. The simulation time may optionally be divided into sequential intervals of time, with displacements of atoms and other parameters of interest calculated for each interval of simulation time. Execution time is a duration of real-world time for a hardware calculating apparatus such as a computer to perform the calculations for a selected duration of simulation time. Real-world time corresponds to time as measured on an ordinary clock. As an example of a short simulation time, a calculation of displacement in accord with an embodiment may be configured for a simulation time of 2 picoseconds may be divided into 1000 time intervals with each time interval representing 2 femtoseconds of real-world time for atoms in motion in a candidate material. With these example parameters, calculation of the displacements of a selected atomic species may be completed in about 0.01 to 0.1 times the computational execution time duration of previously known methods.

When short simulation times are used for displacement calculations, each atom in a structure may make only one or two jumps during the simulation time. Inaccurate diffusivity calculations may result from applying a model comprising a normal distribution to a short simulation time because diffusivity is being estimated from a small amount of displacement data. The higher moments of the distribution, for example skew and kurtosis, are not well approximated by a normal distribution. A normal distribution may also be referred to as a Gaussian distribution. When a normal distribution is applied to data computed for a short simulation time, inaccuracies may appear in values calculated for error bounds and statistical significance. However, in contrast to the embodiments described herein, it has been common practice for previously known methods to apply a normal distribution to diffusivity simulation results. Unfortunately, there may be little indication that a calculation using a normal distribution has produced incorrect results for diffusivity because a normal distribution may give acceptably accurate results for a long simulation time but reduced accuracy for a short simulation time.

Modeling accuracy can be improved by fitting calculated displacement results to a discrete distribution such as a Poisson distribution for describing the number of jumps an atom takes in each direction within a solid-state crystalline structure. A reasonable estimate of jump distance may be based on geometric parameters for the crystal structure, but inaccurate results may be produced when attempting to fit a Poisson distribution, especially for short simulation times. For example, in a one-dimensional system, the number of times each atom jumps to the right or left could be counted. An estimate of parameters for a Poisson distribution may be made from these counts and diffusivity could be determined from the Poisson distribution. However, the Poisson distribution produces inaccurate results for diffusivity when the jumps are not independent of one another or there is a degree of correlation between the jumps, for example when an atom jumps back and forth between two positions but otherwise achieves no net displacement. In this case the Poisson distribution may produce an incorrect high value of diffusivity. Inaccuracies may also be caused by jumps that exceed a correlation distance, where correlation distance represents the distance an atom travels before its new trajectory is uncorrelated with its past trajectory. Increasing the estimate for jump distance could result in none of the jumps in any direction being counted, leading to an incorrect low value of diffusivity. An accurate estimate for jump distance is difficult to determine for small amounts of displacement data.

A Skellam distribution as implemented in the embodiments described herein offers a solution to the correlation problem. In contrast to methods using a Poisson distribution, the Skellam distribution predicts diffusivity by estimating the net motion of atoms. Whereas the estimate of diffusivity is dependent on correlation distance with a Poisson distribution, the error bounds for an estimate resulting from a Skellam distribution are affected by the correlation distance estimate but the estimate of diffusivity is not affected. Accordingly, some embodiments employ a Skellam distribution for determining diffusivity from displacement data for short simulation times, instead of using other distributions such as the Poisson distribution which may produce inaccurate results for short simulation times.

A method in accord with an embodiment begins with receiving selected simulation parameters. Received parameters may include a selection of a candidate material and a structure for the material, for example a geometric description of a crystalline structure. A material may include at least one chemical compound, a mixture of at least two different chemical compounds, or a combination of more than one mixture with each of the mixtures in mechanical contact, and optionally electrical contact, with at least one other mixture in the combination of mixtures. After a material is selected, a simulation of displacements for atoms in the structure is performed at a selected high temperature, for example a temperature of at least 500 Kelvin (K).

Upper and lower bounds for conductivity may be determined from displacement results. If the calculated displacement values have insufficient statistical significance, the displacement simulation may be continued, or may alternatively restart with new parameter choices. When results are determined to have sufficient statistical significance, the displacement simulation may be terminated and the diffusivity or alternately the conductivity of the candidate material compared to a preferred threshold value. A material satisfying the threshold criteria represents a preferred candidate that may be synthesized and tested experimentally or may alternatively be subjected to longer simulation times to improve statistical precision of the computed results. A material which does not satisfy the threshold criteria may be deprioritized from further study. Information about the candidate material may be added to a data store, such as a list, chart, database, etc.

FIG. 1 is a flowchart illustrating an example of a method embodiment 100. In block 102, initial conditions and calculation parameter values are received. Examples of initial conditions and parameter values may include, but are not limited to, a candidate inorganic material, a crystal structure, an atomic species, a temperature value, a threshold value of diffusivity ($D_{th}$), and an initial value for a simulation time duration value (t). The candidate organic material may optionally be selected from a database comprising candidate materials and structures. The atomic species specified is a species whose displacements are to be calculated within the specified crystal structure framework. The atomic species of interest may optionally be selected from a group including lithium, sodium, and magnesium. The temperature value may be a relatively high temperature value, for example a temperature in excess of 500 K. The threshold value may be specified for comparison against computed values of diffusivity. The value of $D_{th}$ may optionally be chosen to represent a corresponding minimum preferred value of ionic conductivity or electrical conductivity. The simulation time duration may initially be a relatively small value to permit rapid screening of candidate materials.

In block 104, displacements of atomic species are calculated relative to crystal lattice reference positions. Displacements may be calculated by methods including, but not limited to, molecular dynamics, ab initio molecular dynamics, and Monte Carlo simulation. A warning notification may optionally be issued when a calculated value of diffusivity indicates that both the selected atomic species and the crystal structure are in motion relative to a stationary reference.

In block 106, an estimate for diffusivity (D) is determined from a Skellam distribution applied to the displacement data. A credible interval may optionally be determined using Bayesian statistics. Alternatively, other statistical analysis techniques may be used to generate a credible interval. Briefly, a credible interval refers to a range in which a true value is likely to occur. Upper and lower bounds for diffusivity, or alternately for conductivity values, may also be determined from the displacement data. Gaussian noise may optionally be included in the calculation of an estimate for D by a Skellam distribution.

In block 108, a determination of whether the precision of the estimate of diffusivity D has sufficient statistical significance is performed. For example, calculated results may be determined to have sufficient statistical significance when the results have converged to within 95% confidence. Alternatively, the calculated results may be determined to have sufficient statistical significance when the results are accurate to within a selected number of significant digits. When the results have been determined to have sufficient statistical significance, the calculation of displacements is terminated as shown in block 110 and the comparison of block 112 is performed. When D is greater than the threshold value $D_{th}$, as shown in block 112, the statistically significant value of D is determined to represent a good conductor and a good candidate for subsequent analysis as suggested in block 114. When the value of D is less than $D_{th}$ the candidate material may be eliminated from further analysis or synthesis and may be added to a knowledge base of poor conductors as suggested in step 116. The method ends after information about the candidate material is added to either the "good conductor" list or "bad conductor" list.

Figure 2:
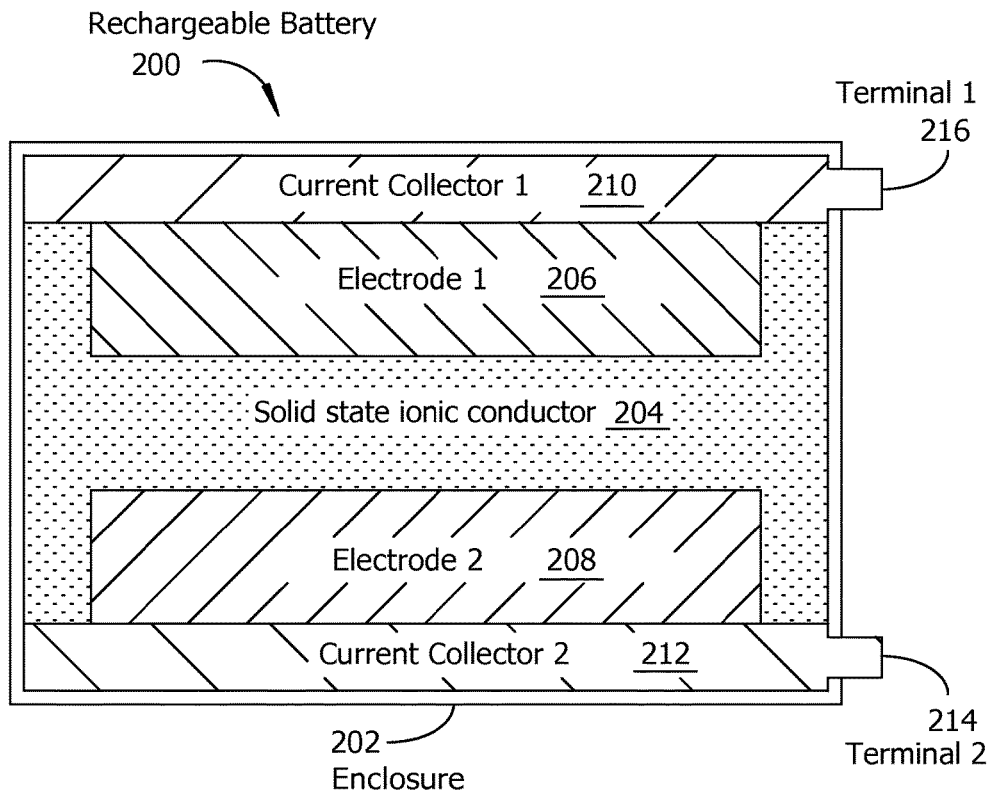
FIG. 2 is a block diagram illustrating an example of an electric storage battery using a solid state ionic conductor selected according to a method embodiment.

FIG. 2 is a simplified representation of a rechargeable electric storage battery embodiment manufactured with a solid state ionic conductor 204 selected according to the example of a method in FIG. 1. The rechargeable battery includes a first electrode 206 and a second electrode 208 in electrical contact with a solid state ionic conductor 204. The solid state ionic conductor 204 is an example of an inorganic compound that is an ionically conductive material. The example of a rechargeable battery 200 may exclude any material in a liquid state inside the battery enclosure 202. The first electrode 206 is electrically connected with a first current collector 210. The second electrode 208 is electrically connected with a second current collector 212. A first electrical terminal 216 electrically connected with the first current collector 210 and a second electrical terminal 214 electrically connected with the second current collector 212 are provided for making electrical connections between the rechargeable battery 200 and an external electrical load (not illustrated).

Figure 3:
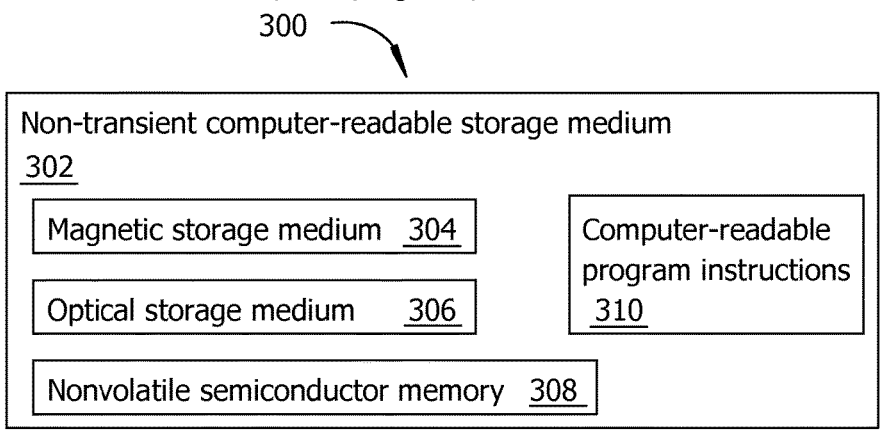
FIG. 3 is a block diagram illustrating an example of a computer program product embodiment including a non-transient computer-readable storage medium.

FIG. 3 illustrates an example of a computer program product embodiment 300 that includes a non-transient computer-readable storage medium 302 storing computer-readable program instructions for executing calculations on a computer system implemented as a hardware apparatus. Computer-readable program instructions 310 may direct the computer system to perform operations in accord with the example of FIG. 1. Examples of a non-transient computer-readable storage medium include, but are not limited to, a magnetic storage medium 304 such as a hard disk or floppy disk, an optical storage medium 306 such as a digital optical disk (e.g., Compact Disk Read-Only Memory (CD ROM), Digital Versatile Disk (DVD), Blu Ray™ Disk (BD), etc.), and a nonvolatile semiconductor memory device 308 such as a memory stick or solid state drive.

Figure 4:
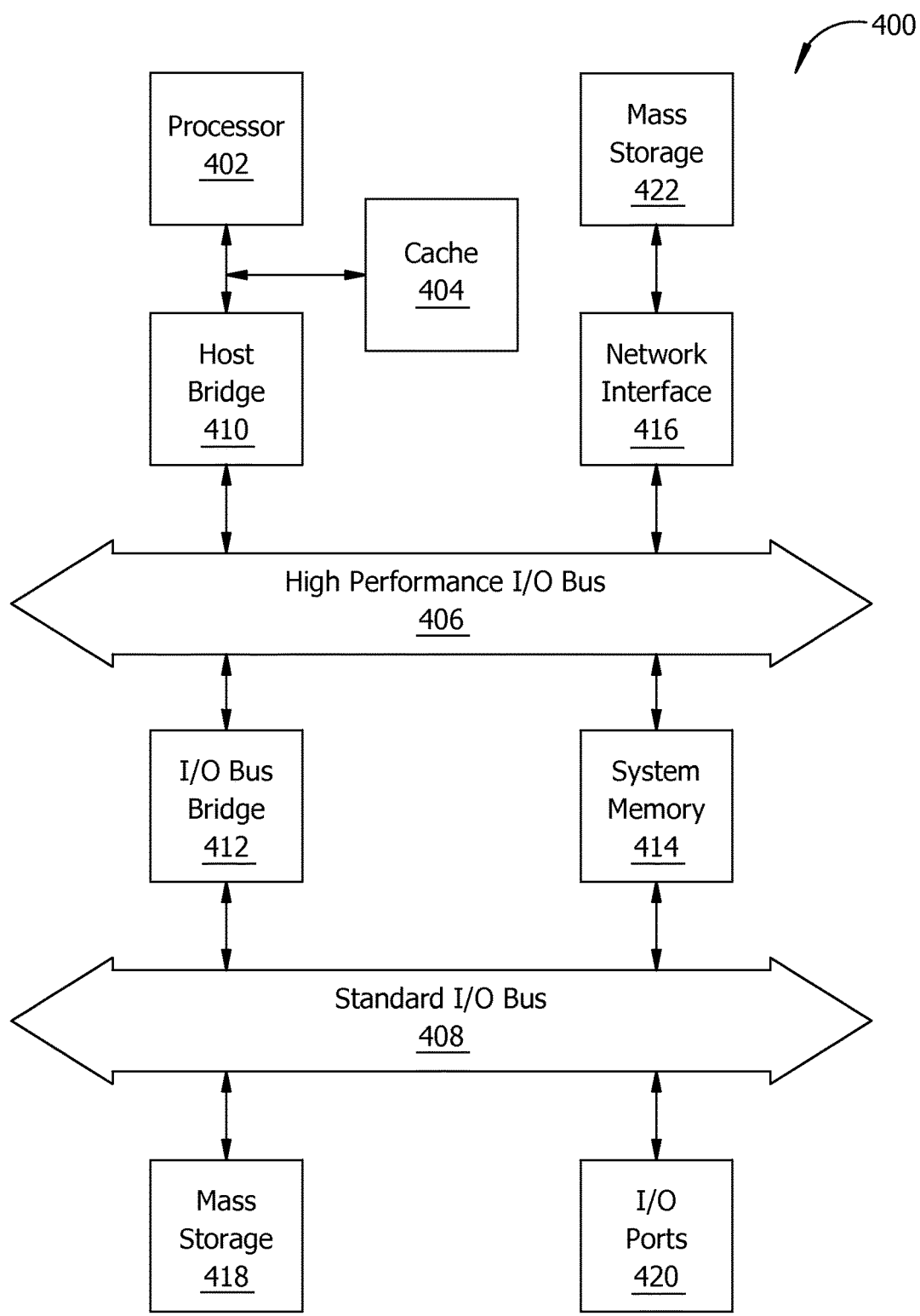
FIG. 4 is a block diagram illustrating an example of an apparatus embodiment including a computer system implemented in hardware.

FIG. 4 illustrates an example of an apparatus embodiment including a computer system 400 that may be used to implement one or more of the embodiments described herein. The example of a computer system 400 includes sets of instructions for causing the computer system 400 to perform the processes and features discussed herein. The computer system 400 may be connected for data communication (e.g., networked) to other machines. In a networked deployment, the computer system 400 may operate in the capacity of a server machine or a client machine in a client-server network environment, or as a peer machine in a peer-to-peer (or distributed) network environment. In an example of an embodiment, the computer system 400 may be a component of the networking system described herein. In another example of an embodiment of the present disclosure, the computer system 400 may be one server among many that constitutes all or part of a networking system.

The computer system 400 includes a processor 402, a cache 404, and one or more executable modules and drivers, stored on a computer-readable medium, directed to the processes and features described herein. Examples of a processor 402 include, but are not limited to, a central processor unit (CPU), a microprocessor, a microcontroller, and a bit slice processor, any of which may be implemented in hardware as electrically interconnected semiconductor devices. The computer system 400 may optionally include more than one processor 402. Additionally, the computer system 400 may include a high performance input/output (I/O) bus 406 or a standard I/O bus 408. A host bridge 410 couples processor 402 to high performance I/O bus 406, whereas I/O bus bridge 412 couples the two buses 406 and 408 to each other. A system memory 414 and one or more network interfaces 416 couple to high performance I/O bus 406. The system memory 414 may optionally include a direct data communication connection to either one or both of the processor 402 and the cache 404. The computer system 400 may further include video memory and a display device coupled to the video memory (not shown).

Mass storage 418 and I/O ports 420 couple to the standard I/O bus 408. Mass storage 418 may optionally be implemented as a nontransient computer-readable storage medium in accord with the example of FIG. 3. Network-attached mass storage 422 may optionally be accessible to the processor 402 through the network interface 416. The computer system 400 may optionally include a keyboard and a pointing device, a display device, or other input/output devices (not shown) coupled to the standard I/O bus 408. Collectively, these elements are intended to represent a broad category of computer hardware systems, including but not limited to computer systems based on the x86-compatible processors manufactured by Intel Corporation of Santa Clara, Calif., and the x86-compatible processors manufactured by Advanced Micro Devices (AMD), Inc., of Sunnyvale, Calif., as well as any other suitable processor.

An operating system manages and controls the operation of the computer system 400, including the input and output of data to and from software applications (not shown). The operating system provides an interface between the software applications being executed on the system and the hardware components of the system. Any suitable operating system may be used, such as the LINUX™ Operating System, available from many sources, the Apple® Macintosh® Operating System, available from Apple Computer Inc. of Cupertino, Calif., UNIX operating systems, Microsoft® Windows® operating systems, BSD operating systems, and the like. Other implementations are possible.

The elements of the computer system 400 are described in greater detail below. In particular, the network interface 416 provides communication between the computer system 400 and any of a wide range of networks, such as an Ethernet (e.g., IEEE 802.3) network, a backplane, etc. The mass storage 418 provides nonvolatile storage for the data and programming instructions to perform the above-described processes and features implemented by the respective computing systems identified above, whereas the system memory 414 provides temporary storage for the data and programming instructions when executed by the processor 402. The system memory 414 may be implemented as electrically interconnected semiconductor devices configured as dynamic random access memory (DRAM). The I/O ports 420 may be one or more serial and/or parallel communication ports that provide communication between additional peripheral devices, which may be coupled to the computer system 400. I/O ports 420 may optionally be configured for bidirectional data communications between the computer system 400 and other devices.

The computer system 400 may include a variety of system architectures, and various components of the computer system 400 may be rearranged. For example, the cache 404 may be on-chip with processor 402. Alternatively, the cache 404 and the processor 402 may be packed together as a "processor module", with processor 402 being referred to as the "processor core". Furthermore, certain embodiments of the invention may neither require nor include all of the above components. For example, peripheral devices coupled to the standard I/O bus 408 may couple to the high performance I/O bus 406. In addition, in certain embodiments, only a single bus may exist, with the components of the computer system 400 being coupled to the single bus. Furthermore, the computer system 400 may include additional components, such as additional processors, storage devices, or memories.

In general, the processes and features described herein may be implemented as part of an operating system or a specific application, component, program, object, module, or series of instructions referred to as "programs". For example, one or more programs may be used to execute specific processes described herein. The programs typically comprise one or more instructions in various memory and storage devices in the computer system 400 that, when read and executed by one or more processors, cause the computer system 400 to perform operations to execute the processes and features described herein. The processes and features described herein may be implemented in software, firmware, hardware (e.g., an application specific integrated circuit), or any combination thereof.

In one implementation, the processes and features described herein are implemented as a series of executable modules run by the computer system 400, individually or collectively in a distributed computing environment. The foregoing modules may be realized by hardware, executable modules stored on a computer-readable medium (or machine-readable medium), or a combination of both. For example, the modules may comprise a plurality or series of instructions to be executed by a processor in a hardware system, such as the processor 402. Initially, the series of instructions may be stored on a storage device, such as the mass storage 418. However, the series of instructions can be stored on any suitable computer readable storage medium. Furthermore, the series of instructions need not be stored locally, and could be received from a remote storage device, such as a server on a network, via the network interface 416. The instructions are copied from the storage device, such as the mass storage 418, into the system memory 414 and then accessed and executed by the processor 402. In various implementations, a module or modules can be executed by a processor or multiple processors in one or multiple locations, such as multiple servers in a parallel processing environment.

Optionally, the foregoing processes and features can be implemented in other similar machine and computer system architectures or in network and computing environments.

Some of the operations described herein may be performed in a different order than implied by the sequence of blocks in FIG. 1. Such variations are considered to be within the scope of the disclosed embodiments.

Unless expressly stated otherwise herein, ordinary terms have their corresponding ordinary meanings within the respective contexts of their presentations, and ordinary terms of art have their corresponding regular meanings.

What is claimed is:

1. A high ionic conductivity solid state screen method, comprising:
   receiving a crystal structure selection for an inorganic material;
   receiving a threshold value selection for diffusivity;
   calculating, by a processor, a displacement of a selected atomic species in the inorganic material relative to the crystal structure;
   calculating, by the processor, an estimate of diffusivity from a Skellam distribution of the displacement;
   comparing the estimate of diffusivity to the threshold value selection for diffusivity;
   identifying the inorganic material as a preferred material when the estimate of diffusivity is greater than or equal to the threshold value selection for diffusivity; and
   providing an indication specifying whether the inorganic material is the preferred material.

2. The method of claim 1, wherein the calculating the displacement comprises a molecular dynamics simulation.

3. The method of claim 1, wherein the calculating the displacement comprises an ab initio molecular dynamics simulation.

4. The method of claim 1, wherein the calculating the displacement comprises a Monte Carlo simulation.

5. The method of claim 1, further comprising determining a value for statistical significance of the estimate of diffusivity, wherein the calculating the displacement continues until the value for statistical significance of the estimate of diffusivity is less than or equal to a threshold value of statistical significance.

6. The method of claim 1, wherein the Skellam distribution is combined with Gaussian noise.

7. The method of claim 1, wherein the threshold value for diffusivity corresponds to a preferred minimum value of electrical conductivity of the inorganic material.

8. The method of claim 1, further comprising receiving a temperature selection greater than or equal to 500 Kelvin for calculating the value of diffusivity.

9. The method of claim 1, further comprising issuing a warning notification when the calculating an estimate of diffusivity indicates that both the selected atomic species and the crystal structure are in motion relative to a stationary reference.

10. The method of claim 1, further comprising:
    calculating, by the processor, an upper bound for diffusivity;
    calculating, by the processor, a lower bound for diffusivity;
    determining, by the processor, a value of convergence for diffusivity from the upper bound and the lower bound; and
    comparing, by the processor, the estimate of diffusivity to the threshold value of diffusivity when the value of convergence corresponds to at least 95 percent confidence in the value of diffusivity.

11. The method of claim 1, further comprising calculating a credible interval of diffusivity from the Skellam distribution of the displacement.

12. A high ionic conductivity solid state screening apparatus comprising:
    a processor; and
    a memory coupled to the processor, the memory including instructions executable by the processor to:
    receive a crystal structure selection for an inorganic material;
    receive a threshold value selection for diffusivity;
    calculate a displacement of a selected atomic species in the inorganic
    material relative to the crystal structure;
    calculate an estimate of diffusivity from a Skellam distribution of the displacement;
    compare the estimate of diffusivity to the threshold value selection for diffusivity;
    identify the inorganic material as a preferred material when the estimate of diffusivity is greater than or equal to the threshold value selection for diffusivity; and
    provide an indication specifying whether the inorganic material is the preferred material.

13. The apparatus of claim 12, wherein the calculation of the displacement is performed by a molecular dynamics simulation.

14. The apparatus of claim 12, wherein the calculation of the displacement is performed by an ab initio molecular dynamics simulation.

15. The apparatus of claim 12, wherein the calculation of the displacement is performed by a Monte Carlo simulation.

16. The apparatus of claim 12, the instructions further comprising:
   determine a value for statistical significance of the estimate of diffusivity; and
   continue the calculating the displacement continues until the value for statistical significance of the estimate of diffusivity is less than or equal to a threshold value of statistical significance.

17. The apparatus of claim 12, wherein the Skellam distribution is combined with Gaussian noise.

18. The apparatus of claim 12, wherein the threshold value for diffusivity corresponds to a preferred minimum value of electrical conductivity of the inorganic material.

19. The apparatus of claim 12, the instructions further comprising issue a warning notification when the calculating an estimate of diffusivity indicates that both the selected atomic species and the crystal structure are in motion relative to a stationary reference.

20. The apparatus of claim 12, the instructions further comprising:
   calculate an upper bound for diffusivity;
   calculate a lower bound for diffusivity;
   determine a value of convergence for diffusivity from the upper bound and the lower bound; and
   compare the estimate of diffusivity to the threshold value of diffusivity when the value of convergence corresponds to at least 95 percent confidence in the value of diffusivity.

21. A non-transitory computer readable storage medium including instructions executable by a processor comprising the steps of:
   receiving a crystal structure selection for an inorganic material;
   receiving a threshold value selection for diffusivity;
   calculating a displacement of a selected atomic species in the inorganic material relative to the crystal structure;
   calculating an estimate of diffusivity from a Skellam distribution of the displacement;
   comparing the estimate of diffusivity to the threshold value selection for diffusivity;
   identifying the inorganic material as a preferred material when the estimate of diffusivity is greater than or equal to the threshold value selection for diffusivity; and
   providing an indication specifying whether the inorganic material is the preferred material.

* * * * *